United States Patent
Boger (10) Patent No.: US 10,610,539 B2
(45) Date of Patent: Apr. 7, 2020

(54) CARDIAC GLYCOSIDE ANALOGS AND THEIR USE IN METHODS FOR INHIBITION OF VIRAL INFECTION

(71) Applicant: THE JOHNS HOPKINS UNIVERSITY, Baltimore, MD (US)

(72) Inventor: Ravit Boger, Baltimore, MD (US)

(73) Assignee: The John Hopkins University, Baltimore, MD (US)

( * ) Notice: Subject to any disclaimer, the term of this patent is extended or adjusted under 35 U.S.C. 154(b) by 320 days.

(21) Appl. No.: 14/900,653

(22) PCT Filed: May 12, 2014

(86) PCT No.: PCT/US2014/037674
§ 371 (c)(1),
(2) Date: Dec. 22, 2015

(87) PCT Pub. No.: WO2014/209507
PCT Pub. Date: Dec. 31, 2014

(65) Prior Publication Data
US 2016/0143934 A1    May 26, 2016

Related U.S. Application Data

(60) Provisional application No. 61/839,655, filed on Jun. 26, 2013.

(51) Int. Cl.
*A61K 31/7048* (2006.01)
(52) U.S. Cl.
CPC ................ *A61K 31/7048* (2013.01)
(58) Field of Classification Search
None
See application file for complete search history.

(56) References Cited

U.S. PATENT DOCUMENTS

2006/0041109 A1    2/2006  Thorson et al.
2008/0220066 A1*   9/2008  Hartley et al. ........... A61K 9/00
                                                       424/486

FOREIGN PATENT DOCUMENTS

EP    0442744       *  8/1991
EP    0442744 A2       8/1991

OTHER PUBLICATIONS

Cai, H., et al., "Digitoxin analogues with improved anticytomegalovirus activity", ACS Medicinal Chemistry Letters, (2014) vol. 5, pp. 395-399.
Elbaz, H., et al., "Digitoxin and its analogs as novel cancer therapeutics", Experimental Hematology & Oncology (2012) vol. 1, No. 4.
Su, C., et al., "Anti-HSV activity of digitoxin and its possible mechanisms", Antiviral Research (2008) vol. 79, pp. 62-70.

* cited by examiner

*Primary Examiner* — Traviss C McIntosh, III
(74) *Attorney, Agent, or Firm* — John Hopkins Technology Ventures (57) ABSTRACT

The present invention provides methods for inhibition of human herpes virus replication in a subject comprising administering to the subject a therapeutically effective amount of a pharmaceutically acceptable composition comprising a cardiac glycoside analog, including for example, a digitoxin analog and pharmaceutically acceptable carrier. Other methods of the present invention include administering a digitoxin analog along with at least one other biologically active compound and pharmaceutically acceptable carrier. Methods for inhibition of the α3 subtype of the Na/K ATPase in a subject comprising administering to the subject a therapeutically effective amount of a pharmaceutically acceptable composition comprising a digitoxin analog are also provided.

19 Claims, 4 Drawing Sheets

CARDIAC GLYCOSIDE ANALOGS AND THEIR USE IN METHODS FOR INHIBITION OF VIRAL INFECTION

REFERENCE TO RELATED APPLICATIONS

This application is a 35 U.S.C. § 371 U.S. national entry of International Application PCT/US2014/037674, having an international filing date of May 12, 2014, which claims the benefit of U.S. Provisional Patent Application No. 61/839,655, filed on Jun. 26, 2013, both of which are hereby incorporated by reference for all purposes as if fully set forth herein.

BACKGROUND OF THE INVENTION

Cardiac glycosides (CGs) have been prescribed for centuries to treat congestive heart failure and arrhythmias, conditions in which they bind to the Na—K-ATPase and inhibit its activity. The number of CGs identified in animals and plants is growing and novel effects are becoming evident, including anti-cancer and anti-viral activities. While the anti-cancer effects have been confirmed in multiple studies, the anti-viral activities have not been well-studied. CGs were reported to inhibit HCMV replication at nM concentration and the present inventors have recently reported that digoxin, and ouabain are potent inhibitors of Towne HCMV replication. HCMV inhibition occurred at an early stage prior to DNA replication, but following binding to its cellular receptors.

Digoxin was reported to inhibit the growth of several cancer cells. A study of breast cancer patients showed that women taking digoxin had a significantly lower death rate compared to those not taking digitalis (6% vs. 34%, respectively). In addition, men who used digoxin regularly, especially users for ≥10 years, had a lower prostate cancer risk. Digoxin and ouabain have been reported to inhibit Herpes Simplex Virus 1 (HSV1) in nanomolar concentrations. Virus entry/attachment was not inhibited, but the expression of viral immediate-early (IE) and early genes was significantly reduced.

Despite recent research, there still exists an unmet need for development of novel anti-herpesvirus drugs which are relatively non-toxic and inhibit viral replication in the host.

SUMMARY OF THE INVENTION

In accordance with an embodiment, the present invention provides a method for inhibition of human herpes virus replication in a subject comprising administering to the subject a therapeutically effective amount of a pharmaceutically acceptable composition comprising a digitoxin analog and pharmaceutically acceptable carrier.

In accordance with another embodiment, the present invention provides a method for inhibition of human herpes virus replication in a cell or population of cells comprising administering to the cell or population of cells an effective amount of a composition comprising a digitoxin analog.

In accordance with a further embodiment, the present invention provides a method for inhibition of human herpes virus replication in a subject comprising administering to the subject a therapeutically effective amount of a pharmaceutically acceptable composition comprising a digitoxin analog, wherein the digitoxin analog is a compound of formula (I):

wherein R comprises one to three reducing sugars selected from the group consisting of a L-sugar, a D-sugar, a deoxy-sugar, a dideoxy-sugar, a glucose epimer, a substituted sugar, a uronic acid, and an oligosaccharide.

In accordance with yet another embodiment, the present invention provides a method for inhibition of human herpes virus replication in a subject comprising administering to the subject a therapeutically effective amount of a pharmaceutically acceptable composition comprising a digitoxin analog, at least one biologically active agent, and pharmaceutically acceptable carrier.

In accordance with a further embodiment, the present invention provides a method for inhibition of the α3 subtype of the Na/K ATPase in a subject comprising administering to the subject a therapeutically effective amount of a pharmaceutically acceptable composition comprising a digitoxin analog, wherein the digitoxin analog is a compound of formula (I):

wherein R comprises one to three reducing sugars selected from the group consisting of a L-sugar, a D-sugar, a deoxy-sugar, a dideoxy-sugar, a glucose epimer, a substituted sugar, a uronic acid, and an oligosaccharide.

BRIEF DESCRIPTION OF THE DRAWINGS

FIG. 3 depicts the cellular toxicity and cell cycle progression of representative digitoxin analogs of the present invention. 3A, MTT assay in HFFs. 3B, Cell cycle by flow cytometry.

DETAILED DESCRIPTION OF THE INVENTION

In accordance with an embodiment, the present invention provides a method for inhibition of human herpes virus in a subject comprising administering to the subject a therapeutically effective amount of a pharmaceutically acceptable composition comprising a digitoxin analog and pharmaceutically acceptable carrier.

The present inventors have found that digitoxin and various analogs of digitoxin inhibit viral replication of the human herpes virus known as human cytomegalovirus (HCMV), which is also known as HHV-5, when administered to a cell or population of cells in an effective amount. In certain embodiments, the cell, or population of cells, are within a host organism or subject.

As used herein, the term "human herpes virus" means DNA viruses from the family Herpesviridae, which are known to infect humans. Examples of species of Herpesviridae include, HSV-1, which causes facial cold-sores (HHV-1), HSV-2 (genital herpes) (HHV-2), Varicella zoster virus, which causes chicken-pox and shingles (HHV-3), Epstein-Barr virus, which causes mononucleosis (glandular fever) (HHV-5), HCMV, cytomegalovirus (HHV-5), Roseolovirus (HHV-6A), Herpes lymphotrophic virus (HHV-6B), Pityriasis Rosea (HHV-7), and Kaposi's sarcoma-associated herpesvirus (HHV-8).

The term "digitoxin analog" as used herein, means, in some embodiments, a compound of formula (I):

(I)

wherein R comprises one to three reducing sugars selected from the group consisting of a L-sugar, a D-sugar, a deoxy-sugar, a dideoxy-sugar, a glucose epimer, a substituted sugar, a uronic acid, and an oligosaccharide.

In some embodiments, R can have, two reducing sugars. In other embodiments, R can have three reducing sugar moieties. When the compound of formula I has two or more reducing sugars, it will be understood that the sugars are chemically linked via their reducing ends, and can be the same or different sugar moieties.

In accordance with some embodiments, the reducing sugars of the compound of formula I can have the following formula:

(II)

wherein $R_1$, $R_2$, $R_3$, and $R_4$ are independently selected from —H, —OH, —N$_3$, —NH$_2$, —CH$_3$, —CH$_2$OH, —CN$_3$, —CH$_2$NH, —CH$_2$SH, —CNH$_2$, —CH$_2$N$_3$, —COOH, —COCH$_3$, —CXH$_2$, —CX$_2$H, and wherein X is Cl, Br, F, or I.

In accordance with one or more embodiments, the reducing sugars of R can be the same or different, and are selected from the group consisting of L-amicetose, D-amicetose, L-rhamnose, D-rhamnose, L-ribose, D-ribose, L-fucose, D-fucose, 2-deoxy-D-galactose, 3-deoxy-D-glucose, 6-deoxy-D-glucose, 2-deoxy-2-fluoro-D-glucose, 6-deoxy-6-fluoro-D-glucose, L-lyxose, D-lyxose, L-rhamnose, L-allose, D-allose, L-altrose, D-altrose, L-galactose, D-galactose, L-xylose, D-xylose, D-gulose, L-mannose, D-mannose, L-idose, D-idose, L-mycarose, 6-keto-D-galactose, L-arabinose, D-arabinose, N-acetyl-D-galactosaminose, melibiose, lactose, maltose, D-galacturonose, L-talose, D-talose, 6-deoxy-6-azo-D-mannose, L-glucose, and D-glucose.

In some embodiments the present invention provides methods of treatment using a digitoxin analog of formula I, wherein R is selected from the group consisting of: α-L-amicetose, bis-L-amicetose, tris-L-amicetose, α-D-amicetose, bis-D-amicetose, tris-D-amicetose, α-L-rhamnose, bis-L-rhamnose, tris-L-rhamnose, α-D-rhamnose, bis-D-rhamnose, tris-D-rhamnose, and D-mannose.

As such, in accordance with an embodiment, the present invention provides a composition comprising a digitoxin analog and a pharmaceutically acceptable carrier for use as a medicament, preferably for use in the inhibition of human herpes virus replication in a subject. In another embodiment, the present invention provides a composition comprising a digitoxin analog, at least one additional biologically active agent, and a pharmaceutically acceptable carrier for use as a medicament, preferably for use in the inhibition of human herpes virus replication in a subject.

One of ordinary skill in the art will understand that digitoxin is a member of the cardiotonic steroid or cardiotonic glycoside family of compounds. The cardiac glycosides are an important class of naturally occurring drugs whose actions include both beneficial and toxic effects on the heart. Plants containing cardiac steroids have been used as poisons and heart drugs at least since 1500 B.C. Throughout history these plants or their extracts have been variously used as arrow poisons, emetics, diuretics, and heart tonics. Cardiac steroids are widely used in the modern treatment of congestive heart failure and for treatment of atrial fibrillation and flutter. The R group at the 17-position defines the class of cardiac glycoside. Two classes have been observed in nature, the cardenolides, and the bufadienolides. The cardenolides have an unsaturated butyrolactone ring while the bufadienolides have an a-pyrone ring. The steroid nucleus has hydroxyls at 3- and 14-positions of which the sugar attachment uses the 3-OH group. 14-OH is normally unsubstituted. Many genins have OH groups at 12- and 16-positions. These additional hydroxyl groups influence the partitioning of the cardiac glycosides into the aqueous media and greatly affect the duration of action. The lactone moiety at C-17 position is an important structural feature. The size and degree of unsaturation varies with the source of the glycoside. Normally plant sources provide a 5-membered unsaturated lactone while animal sources give a 6-membered unsaturated lactone.

One to four sugars are found to be present in most cardiac glycosides attached to the 3β-OH group. The sugars most commonly used include L-rhamnose, D-glucose, D-digitoxose, D-digitalose, D-digginose, D-sarmentose, L-vallarose, and D-fructose. These sugars predominantly exist in the cardiac glycosides in the β-conformation. The presence of acetyl group on the sugar affects the lipophilic character and the kinetics of the entire glycoside.

Accordingly, included within the compounds of the present invention are the tautomeric forms of the disclosed compounds, isomeric forms including enantiomers, stereoisomers, and diastereoisomers, and the pharmaceutically-acceptable salts thereof. The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the present invention include, for example, acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present invention.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds of the present invention should be pharmaceutically acceptable salts. Other salts may, however, be useful in the preparation of the compounds according to the invention or of their pharmaceutically acceptable salts.

In addition, embodiments of the invention include hydrates of the compounds of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

"Treating" or "treatment" is an art-recognized term which includes curing as well as ameliorating at least one symptom of any condition or disease. Treating includes reducing the likelihood of a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder or condition, e.g., causing any level of regression of the disease; inhibiting the disease, disorder or condition, e.g., impeding its progress; and relieving the disease, disorder or condition, even if the underlying pathophysiology is not affected or other symptoms remain at the same level. In accordance with some embodiments, the digitoxin analogs of the present invention are useful in the treatment of human herpes viral infection, including, for example, prevention of HHV-5/HCMV replication.

Without being held to any particular theory, the present inventors believe that the digitoxin analogs of the present invention have an inhibitory effect on the α3 subtype of Na/K ATPase enzyme (ATP1A3 gene) on the cell membrane. As such, in accordance with an embodiment, the present invention provides a method for inhibition of the α3 subtype of the Na/K ATPase in a subject comprising administering to the subject a therapeutically effective amount of a pharmaceutically acceptable composition comprising a digitoxin analog, wherein the digitoxin analog is a compound of formula (I):

wherein R comprises one to three reducing sugars selected from the group consisting of a L-sugar, a D-sugar, a deoxy-sugar, a dideoxy-sugar, a glucose epimer, a substituted sugar, a uronic acid, and an oligosaccharide.

As such, in accordance with an embodiment, the present invention provides a composition comprising a digitoxin analog and a pharmaceutically acceptable carrier for use as a medicament, preferably for use for inhibition of the α3 subtype of the Na/K ATPase in a subject.

In accordance with an embodiment, the present invention provides a pharmaceutical composition comprising a digitoxin analog, wherein the digitoxin analog is a compound of formula (I):

wherein R comprises one to three reducing sugars selected from the group consisting of a L-sugar, a D-sugar, a deoxy-sugar, a dideoxy-sugar, a glucose epimer, a substituted sugar, a uronic acid, and an oligosaccharide, and a pharmaceutically acceptable carrier for use as a medicament, preferably for use as an antiviral agent and/or inhibition of the α3 subtype of the Na/K ATPase in a subject.

In some embodiments, reducing sugars used in the pharmaceutical compositions of the present invention are the same or different and are selected from the group consisting of L-amicetose, D-amicetose, L-rhamnose, D-rhamnose, L-ribose, D-ribose, L-fucose, D-fucose, 2-deoxy-D-galactose, 3-deoxy-D-glucose, 6-deoxy-D-glucose, 2-deoxy-2-fluoro-D-glucose, 6-deoxy-6-fluoro-D-glucose, L-lyxose, D-lyxose, L-rhamnose, L-allose, D-allose, L-altrose, D-altrose, L-galactose, D-galactose, L-xylose, D-xylose, D-gulose, L-mannose, D-mannose, L-idose, D-idose, L-mycarose, 6-keto-D-galactose, L-arabinose, D-arabinose, N-acetyl-D-galactosaminose, melibiose, lactose, maltose, D-galacturonose, L-talose, D-talose, 6-deoxy-6-azo-D-mannose, L-glucose, and D-glucose.

In certain embodiments, the digitoxin analogs in the pharmaceutical compositions disclosed herein are selected from the group consisting of α-L-amicetose, Bis-L-amicetose, Tris-L-amicetose, α-D-amicetose, Bis-D-amicetose, Tris-D-amicetose, α-L-rhamnose, Bis-L-rhamnose, Tris-L-rhamnose, α-D-rhamnose, Bis-D-rhamnose, Tris-D-rhamnose, and D-mannose.

In some embodiment, the pharmaceutical compositions disclosed herein are useful for treating viral infections in a subject. In some preferred embodiment, the viral infection is a herpes virus infection.

In some embodiments, the pharmaceutical compositions disclosed herein can be combined with one or more additional therapeutic agents, including, for example, anti-viral agents.

"Prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The compositions of the present invention may include a carrier. The term, "carrier," refers to a diluent, adjuvant, excipient or vehicle with which the therapeutic is administered. Such physiological carriers can be sterile liquids, such as water and oils, including those of petroleum, animal, vegetable or synthetic origin, such as peanut oil, soybean oil, mineral oil, sesame oil and the like. Water is a suitable carrier when the pharmaceutical composition is administered intravenously. Saline solutions and aqueous dextrose and glycerol solutions also can be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The compositions, if desired, can also contain minor amounts of wetting or emulsifying agents, or pH buffering agents.

The compositions of the present invention may include a surfactant. As used herein, the term "surfactant" refers to organic substances having amphipathic structures, namely, are composed of groups of opposing solubility tendencies, typically an oil-soluble hydrocarbon chain and a water-soluble ionic group. Surfactants can be classified, depending on the charge of the surface-active moiety, into anionic, cationic and nonionic surfactants. Surfactants often are used as wetting, emulsifying, solubilizing and dispersing agents for various pharmaceutical compositions and preparations of biological materials.

The digitoxin analogs used in the methods of the present invention may also include an additional active agent. An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc. In some embodiments, the active agent is an anti-viral agent, such as ganciclovir.

Examples of other antiviral agents which can be used with the digitoxin analogs in the methods of the present invention include, but are not limited to, Acyclovir, Amantadine, Atazanavir, Cidofovir, Didanosine, Emtricitabine, Famciclovir, Ibacitabine, Indinavir, Lamivudine, Nelfinavir, Ribavirin, Saquinavir, Tea tree oil, Vidarabine, and Zidovudine.

The digitoxin analogs used in the methods of the present invention may include pharmaceutically acceptable salts. Pharmaceutically acceptable salts are art-recognized, and include relatively non-toxic, inorganic and organic acid addition salts of compositions of the present invention, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di-, or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenthylamine; (trihydroxymethyl) aminoethane; and the like, see, for example, J. Pharm. Sci., 66: 1-19 (1977).

In one aspect of this invention, a composition comprising a digitoxin analog and one or more biologically active agents may be prepared. The biologically active agent may vary widely with the intended purpose for the composition. The term "active" is art-recognized and refers to any moiety that is a biologically, physiologically, or pharmacologically active substance that acts locally or systemically in a subject. Examples of biologically active agents, that may be referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a biologically active agent may be used which are capable of being released the subject composition, for example, into adjacent tissues or fluids upon administration to a subject.

In certain embodiments, the subject compositions of the present invention comprise about 1% to about 75% or more by weight of the total composition, alternatively about 2.5%, 5%, 10%, 20%, 30%, 40%, 50%, 60% or 70%, of a biologically active agent.

Various forms of the biologically active agents may be used. These include, without limitation, such forms as uncharged molecules, molecular complexes, salts, ethers, esters, amides, prodrug forms and the like, which are biologically activated when implanted, injected or otherwise placed into a subject.

In certain embodiments of the present invention, other materials may be incorporated into subject compositions in addition to one or more biologically active agents. For example, plasticizers and stabilizing agents known in the art may be incorporated in compositions of the present invention. In certain embodiments, additives such as plasticizers and stabilizing agents are selected for their biocompatibility or for the resulting physical properties of the reagents.

Buffers, acids and bases may be incorporated in the compositions of the present invention to adjust pH. Agents to increase the diffusion distance of agents released from the composition may also be included.

The charge, lipophilicity or hydrophilicity of a composition of the present invention may be modified by employing an additive. For example, surfactants may be used to enhance miscibility of poorly miscible liquids. Examples of suitable surfactants include dextran, polysorbates and sodium lauryl sulfate. In general, surfactants are used in low concentrations, generally less than about 5%.

Therapeutic formulations of the compositions of the present invention may be prepared for storage as lyophilized formulations or aqueous solutions by mixing the product having the desired degree of purity with optional pharmaceutically acceptable carriers, diluents, excipients or stabilizers typically employed in the art, i.e., buffering agents, stabilizing agents, preservatives, isotonifiers, non-ionic detergents, antioxidants and other miscellaneous additives, see Remington's Pharmaceutical Sciences, 16th ed., Osol, ed. (1980). Such additives are generally nontoxic to the recipients at the dosages and concentrations employed, hence, the excipients, diluents, carriers and so on are pharmaceutically acceptable.

The compositions of the present invention can take the form of solutions, suspensions, emulsions, powders, sustained-release formulations, depots and the like. Examples of suitable carriers are described in "Remington's Pharmaceutical Sciences," Id. Such compositions will contain an effective amount of the biopolymer of interest, preferably in purified form, together with a suitable amount of carrier so as to provide the form for proper administration to the patient. As known in the art, the formulation will be constructed to suit the mode of administration.

Buffering agents help to maintain the pH in the range which approximates physiological conditions. Buffers are preferably present at a concentration ranging from about 2 mM to about 50 mM. Suitable buffering agents for use with the instant invention include both organic and inorganic acids, and salts thereof, such as citrate buffers (e.g., monosodium citrate-disodium citrate mixture, citric acid-trisodium citrate mixture, citric acid-monosodium citrate mixture etc.), succinate buffers (e.g., succinic acid monosodium succinate mixture, succinic acid-sodium hydroxide mixture, succinic acid-disodium succinate mixture etc.), tartrate buffers (e.g., tartaric acid-sodium tartrate mixture, tartaric acid-potassium tartrate mixture, tartaric acid-sodium hydroxide mixture etc.), fumarate buffers (e.g., fumaric acid-monosodium fumarate mixture, fumaric acid-disodium fumarate mixture, monosodium fumarate-disodium fumarate mixture etc.), gluconate buffers (e.g., gluconic acid-sodium gluconate mixture, gluconic acid-sodium hydroxide mixture, gluconic acid-potassium gluconate mixture etc.), oxalate buffers (e.g., oxalic acid-sodium oxalate mixture, oxalic acid-sodium hydroxide mixture, oxalic acid-potassium oxalate mixture etc.), lactate buffers (e.g., lactic acid-sodium lactate mixture, lactic acid-sodium hydroxide mixture, lactic acid-potassium lactate mixture etc.) and acetate buffers (e.g., acetic acid-sodium acetate mixture, acetic acid-sodium hydroxide mixture etc.). Phosphate buffers, carbonate buffers, histidine buffers, trimethylamine salts, such as Tris, HEPES and other such known buffers can be used.

Preservatives may be added to the compositions of the present invention to retard microbial growth, and may be added in amounts ranging from 0.2%-1% (w/v). Suitable preservatives for use with the present invention include phenol, benzyl alcohol, m-cresol, octadecyldimethylbenzyl ammonium chloride, benzyaconium halides (e.g., chloride, bromide and iodide), hexamethonium chloride, alkyl parabens, such as, methyl or propyl paraben, catechol, resorcinol, cyclohexanol and 3-pentanol.

Isotonicifiers can be present to ensure physiological isotonicity of liquid compositions of the instant invention and include polhydric sugar alcohols, preferably trihydric or higher sugar alcohols, such as glycerin, erythritol, arabitol, xylitol, sorbitol and mannitol. Polyhydric alcohols can be present in an amount of between about 0.1% to about 25%, by weight, preferably 1% to 5% taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols; amino acids, such as arginine, lysine, glycine, glutamine, asparagine, histidine, alanine, ornithine, L-leucine, 2-phenylalanine, glutamic acid, threonine etc.; organic sugars or sugar alcohols, such as lactose, trehalose, stachyose, arabitol, erythritol, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, a-monothioglycerol and sodium thiosulfate; low molecular weight polypeptides (i.e., <10 residues); proteins, such as human serum albumin, bovine serum albumin, gelatin or immunoglobulins; hydrophilic polymers, such as polyvinylpyrrolidone, saccharides, monosaccharides, such as xylose, mannose, fructose or glucose; disaccharides, such as lactose, maltose and sucrose; trisaccharides, such as raffinose; polysaccharides, such as, dextran and so on.

Additional miscellaneous excipients include bulking agents, (e.g., starch), chelating agents (e.g., EDTA), antioxidants (e.g., ascorbic acid, methionine or vitamin E) and cosolvents.

Non-ionic surfactants or detergents (also known as "wetting agents") may be added to help solubilize the therapeutic agent, as well as to protect the therapeutic protein against agitation-induced aggregation, which also permits the formulation to be exposed to shear surface stresses without causing denaturation of the protein. Suitable non-ionic surfactants include polysorbates (20, 80 etc.), polyoxamers (184, 188 etc.), Pluronic® polyols and polyoxyethylene sorbitan monoethers (TWEEN-20®, TWEEN-80® etc.). Non-ionic surfactants may be present in a range of about 0.05 mg/ml to about 1.0 mg/ml, preferably about 0.07 mg/ml to about 0.2 mg/ml.

The instant invention encompasses formulations, such as, liquid formulations having stability at temperatures found in a commercial refrigerator and freezer found in the office of a physician or laboratory, such as from about 20° C. to about 5° C., said stability assessed, for example, by microscopic analysis, for storage purposes, such as for about 60 days, for about 120 days, for about 180 days, for about a year, for about 2 years or more. The liquid formulations of the present invention also exhibit stability, as assessed, for example, by particle analysis, at room temperatures, for at least a few hours, such as one hour, two hours or about three hours prior to use.

Examples of diluents include a phosphate buffered saline, buffer for buffering against gastric acid in the bladder, such as citrate buffer (pH 7.4) containing sucrose, bicarbonate buffer (pH 7.4) alone, or bicarbonate buffer (pH 7.4) containing ascorbic acid, lactose, or aspartame. Examples of carriers include proteins, e.g., as found in skim milk, sugars, e.g., sucrose, or polyvinylpyrrolidone. Typically these carriers would be used at a concentration of about 0.1-90% (w/v) but preferably at a range of 1-10%

The formulations to be used for in vivo administration must be sterile. That can be accomplished, for example, by filtration through sterile filtration membranes. For example, the formulations of the present invention may be sterilized by filtration.

The digitoxin analogs and compositions of the present invention can be administered to a patient at therapeutically effective doses to prevent, treat, or control the condition, such as a viral infection. The compounds are administered to a patient in an amount sufficient to elicit an effective protective or therapeutic response in the patient. An effective therapeutic response is a response that at least partially arrests or slows the symptoms or complications of the disease. An amount adequate to accomplish this is defined as "therapeutically effective dose." The dose will be determined by the efficacy of the particular digitoxin analog and/or biologic agent employed and the condition of the subject, as well as the body weight or surface area of the area to be treated. The size of the dose also will be determined by the existence, nature, and extent of any adverse effects that accompany the administration of a particular compound in a particular subject.

The choice of carrier will be determined, in part, by the particular compound, as well as by the particular method used to administer the digitoxin analogs of formula I. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compounds, and in certain instances, a particular route can provide a more immediate and more effective response than another route.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

The dose of the compounds, salts, solvates, or stereoisomers of any one the compounds of formula I, as set forth above, of the present invention also will be determined by the existence, nature and extent of any adverse side effects that might accompany the administration of a particular compound. Typically, an attending physician will decide the dosage of the compound with which to treat each individual patient, taking into consideration a variety of factors, such as age, body weight, general health, diet, sex, compound to be administered, route of administration, and the severity of the condition being treated. By way of example, and not intending to limit the invention, the dose of the compounds of the present invention should achieve serum levels within about 1 ng/ml to about 100 ng/ml, including concentrations of 15, 20, 25, 30, 35, 40, 50, 60, 80, and 90 ng/ml, preferably about 10 ng/ml to about 50 ng/ml. In some embodiments, the dose of the compounds of the present invention should be about 30 ng/ml to about 40 ng/ml.

As defined herein, in one or more embodiments, "contacting" means that the one or more compounds of the present invention are introduced into a sample having at least one cell or population of cells infected with a virus, such as HCMV, and appropriate enzymes or reagents, in a test tube, flask, tissue culture, chip, array, plate, microplate, capillary, or the like, and incubated at a temperature and time sufficient to permit binding and uptake of the at least one compound into the cell. Methods for contacting the samples with the compounds, and other specific binding components are known to those skilled in the art, and may be selected depending on the type of assay protocol to be run. Incubation methods are also standard and are known to those skilled in the art.

The population of cells can be a heterogeneous population comprising the host cell comprising any of the compounds of formula I described, in addition to at least one other cell, e.g., a host cell (e.g., a epithelial cell), which does not comprise any of the nanoparticles, or a cell other than a epithelial cell, e.g., a macrophage, a neutrophil, an erythrocyte, a hepatocyte, a hepatic stellate cell, an endothelial cell, an epithelial cell, a muscle cell, a brain cell, etc. Alternatively, the population of cells can be a substantially homogeneous population, in which the population comprises mainly of host cells (e.g., consisting essentially of) comprising the compounds of formula I.

In another embodiment, the term "contacting" means that the at least one compound of the present invention is introduced into a subject, and the at least one compounds is allowed to come in contact with the human herpes virus infected cell or population of cells in vivo.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

EXAMPLES

Compounds: Digitoxin and ganciclovir (GCV) were purchased from Sigma Chemicals, (St. Louis, Mo.). The digitoxin analogs: α-L-amicetose, bis-L-amicetose, tris-L-amicetose, α-D-amicetose, bis-D-amicetoe, tris-D-amicetose, α-L-rhamnose, bis-L-rhamnose, tris-L-rhamnose, a-D-rhamnose, bis-D-rhamnose, tris-D-rhamnose and mannose were previously described (see, Table 1 for compound structures) (ACS Med Chem Lett 2: 264-269 (2011); Curr Top Med Chem 8: 114-125 (2008)). All compounds were dissolved in dimethyl sulfoxide (DMSO), except for GCV which was dissolved in distilled water. 10 mM stock solutions were stored in −80° C.

TABLE 1

Structure of Digitoxin analogs

| Compound | Structure |
| --- | --- |
| digitoxin | |
| mannose | |
| α-L-amicetose | |
| α-L-rhamnose | |
| Bis-L-amicetose | |
| Bis-L-rhamnose | |
| Tris-L-amicetose | |

TABLE 1-continued

Structure of Digitoxin analogs

| Compound | Structure |
|---|---|
| Tris-L-rhamnose | (structure) |
| α-D-amicetose | (structure) |
| α-D-rhamnose | (structure) |
| Bis-D-amicetose | (structure) |
| Bis-D-rhamnose | (structure) |
| Tris-D-amicetose | (structure) |
| Tris-D-rhamnose | (structure) |

Viruses: The recombinant pp28-luciferase HCMV Towne strain was constructed as previously described (Virol J., 8:40 (2011)). This virus expresses luciferase under the control of the pp28 late promoter. Luciferase expression is strongly activated 48-72 hours post infection (hpi). This reporter system is sensitive, reproducible and highly correlates with plaque reduction. HCMV strain-TB40 with a plasmid carrying the UL32 gene fused to GFP was obtained from ATCC (ATCC VR-1578).

Cell culture, human herpes virus infection and anti-viral assays. Human Foreskin Fibroblasts (HFFs) passage 12-16 (ATCC, CRL-2088™) were grown in Dulbecco's Modified Eagle Medium (DMEM) containing 10% fetal bovine serum (FBS) (Gibco, Carlsbad, Calif.) in a 5% $CO_2$ incubator at 37° C. and used for infection with HCMV at multiplicity of infection of 1 PFU/cell (MOI=1). Following 90 minute adsorption, media was removed and cells were washed with PBS. DMEM with 4% FBS containing compounds was added to each well. Infected, treated HFFs were collected at 72 hpi and lysates were assayed for luciferase using a luciferase assay kit (Promega, Madison, Wis.) on GloMax®-Multi+Detection System (Promega) according to manufacturer's instructions.

The inhibitory effects of digitoxin analogs on HCMV yield was determined by real-time PCR. DNA was isolated from supernatants of infected treated cells at 96 hpi. The real-time PCR is based on detection of the highly conserved US17 gene. The limit of detection of the assay is 100 copies/mL (3.0 copies/reaction), and the measureable range is 2.4-8.0 log 10 copies/mL. The PCR was performed using a total reaction volume of 50 µL, including TaqMan 2× Universal PCR Master Mix (Applied Biosystems, Foster City, Calif.), primers (300 nM final concentration), FAM-labeled probe (200 nM final concentration), dH20, and template (10 µl). Amplification was performed on a 7500 Real-Time PCR System (Applied Biosystems, Foster City, Calif.). PCR conditions were: 50° C. for 2 minutes, 95° C. for 10 minutes, 40 cycles of 95° C. for 15 seconds and 60° C. for 60 seconds. Quantification standards were prepared by cloning the US17 amplicon in the pCR®2.1-TOPO® plasmid vector (Invitrogen, Carlsbad, Calif.). Serial 10-fold dilutions of plasmid from 7.0 to 1.0 $log_{10}$ copies/reaction were included with each assay and used to establish a standard curve. Assay controls included quantified CMV AD169 DNA (Advanced Biotechnologies Inc.) and quantified Towne CMV at 3.0 and 5.0 $log_{10}$ copies/mL. Quantitative CMV data were expressed as viral DNA copies per milliliter.

A plaque assay was performed with HCMV Towne virus. The virus was diluted to a desired concentration which gave 50-60 plaques per well. Medium was aspirated from the wells, and 0.2 ml of virus suspension was added to each well in triplicates. Plates were incubated for 90 minutes with shaking every 10 minutes, thereafter compounds were added and a methylcellulose overlay applied to each well. After incubation for 7 days, cells were stained with crystal violet. The stain was aspirated, wells were washed with phosphate-buffered saline, and plaques were counted.

Cell viability. Cell viability was determined using a colorimetric MTT cell proliferation assay following manufacturer's instructions (Sigma-Aldrich, St. Louis, Mo.). HFFs were treated with varying concentrations of the digitoxin analogs of the present invention and incubated at 37° C. for 3 days. After the addition of 20 µl/well of MTT (3-(4,5-Dimethyl-2-thiazolyl)-2,5-diphenyl-2H-tetrazolim bromide) (5 mg/ml in PBS), and shaking at 150 rpm for 5 minutes, the plates were incubated at 37° C. for 3 hours. Conversion of yellow solution into dark blue formazan by mitochondrial dehydrogenases of living cells was quantified by measuring absorbance at 570 nM. Viable cells in culture medium containing vehicle alone (0.1% DMSO) were referred to as 100% cell viability. For each cell type used for virus infection and drug treatment, the MTT assay was performed at the same time points as the antiviral assay. Trypan blue staining was also carried out to determine whether the MTT test which is dependent on enzyme activity correlates with cell viability.

Flow Cytometry: $1 \times 10^5$ HFFs from infected-treated or untreated conditions were washed with cold PBS. Cells were suspended in 70% pre-cooled alcohol. Cells were permeabilized in −20° C. for at least 2 hours followed by centrifugation at 5000 rpm for 5 minutes. The supernatants were discarded and cells were washed with cold PBS three times. Cells were re-suspended in 500 ul PBS, propidium iodide was added to a final concentration of 20-50 µg/ml and cells were incubated at room temperature for at least 10 minutes before applying them on flow machine.

Example 1

Figure 1:
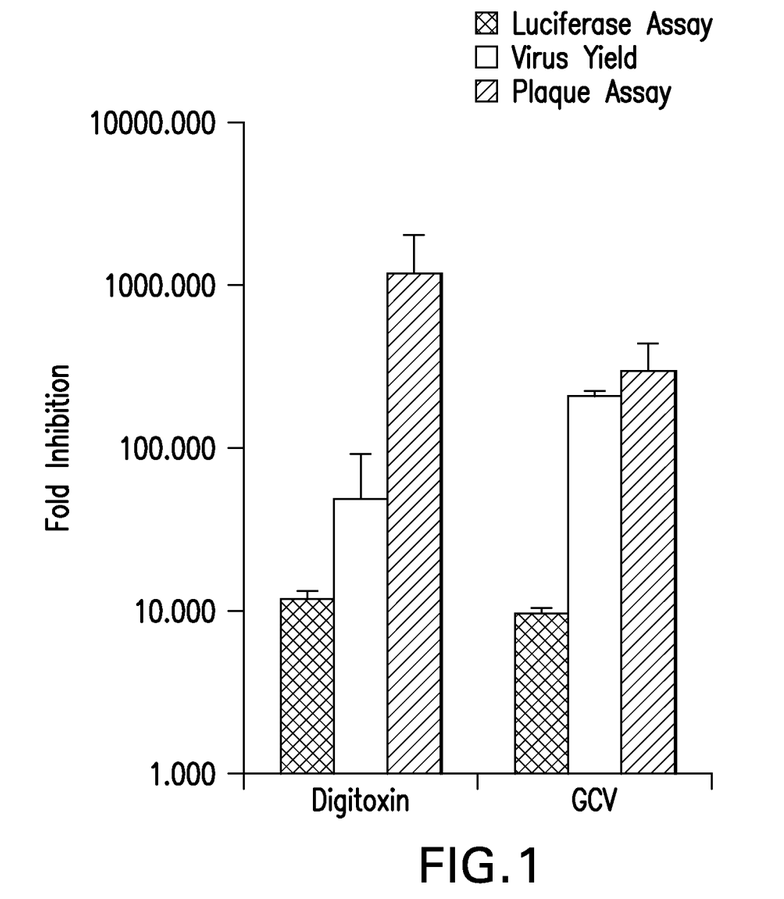
FIG. 1 is a graph showing inhibition of Towne HCMV replication with digitoxin and ganciclovir.

The inhibition of HCMV replication by digitoxin was tested. At 50 nM, digitoxin inhibited HCMV replication similar to GCV (5 µM) based on the following anti-viral assays: pp28 expression (by luciferase), virus DNA yield (by real-time PCR) and plaque reduction of HCMV Towne and by GFP signal of HCMV-TB40 strain (FIG. 1).

Example 2

Figure 2A:
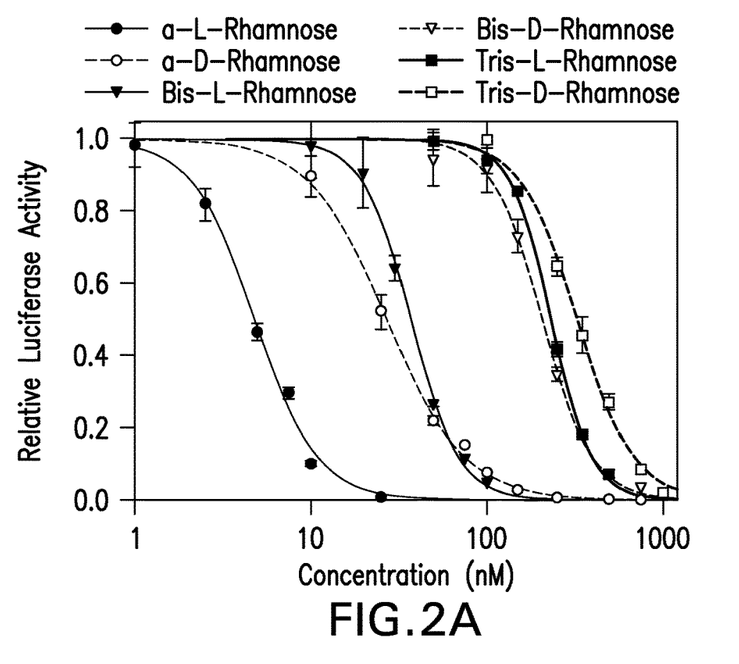
Figure 2B:
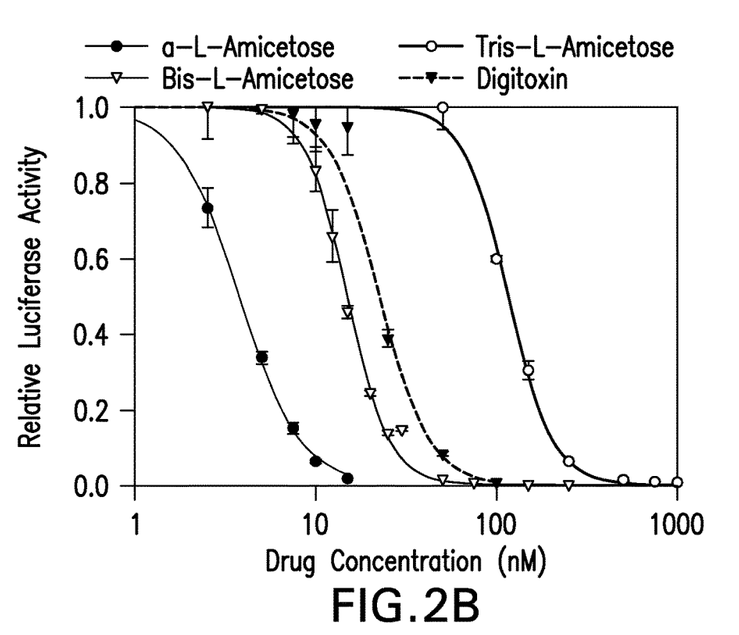
Figure 2C:
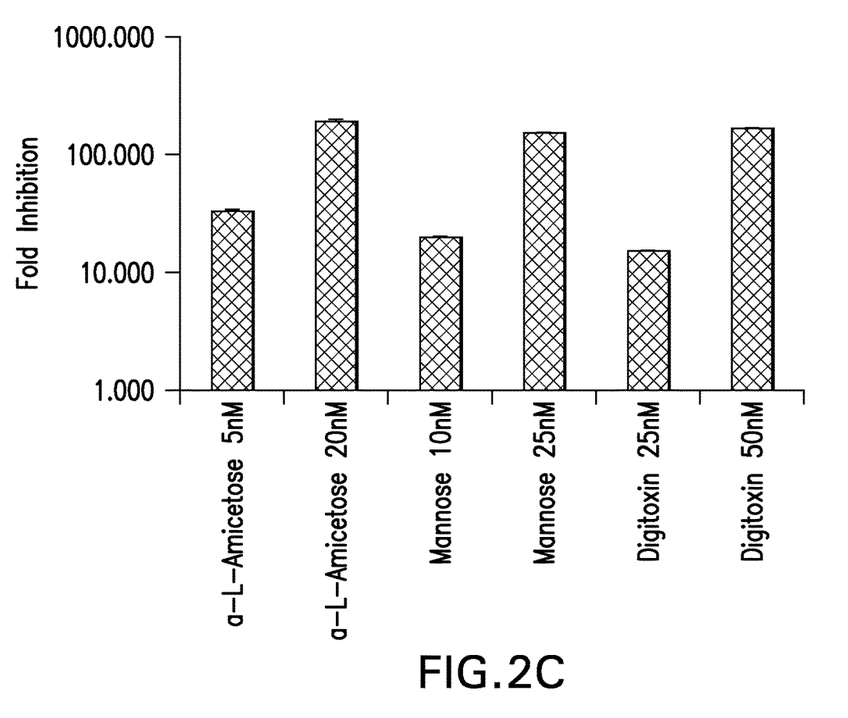
FIG. 2 depicts the anti-HCMV activity of the digitoxin analogs of the present invention. 2A, Dose response curve of rhamnose (left) and amicetose (right). 2B, Virus DNA yield of digitoxin analogs by real-time PCR.

The effect of digitoxin analogs on HCMV replication was tested. HFFs were infected with pp28-luciferase HCMV and treated with the compounds (Table 2, FIG. 2A). $EC_{50}$, $CC_{50}$ and selectivity index (SI) calculated as $CC_{50}/EC_{50}$ were determined for each compound. The L-isomers had an improved anti-HCMV activity compared to the D-isomers. Within each stereoisomer, there was an inverse correlation between the sugar length and anti-HCMV activity; the longer the oligosaccharide chain, the less effective the compound was against HCMV replication. There was also decreased cytotoxicity in HFFs as the sugar length increased; however, the anti-HCMV activity was not a result of cytotoxicity as reflected by the selectivity index (SI). The compounds with the best SI were α-L rhamnose, α-L amicetose and mannose. Virus yield was determined for selected compounds (FIG. 2B), and a dose dependent effect on virus DNA yield was observed.

TABLE 2

$EC_{50}$, $CC_{50}$ and selectivity index (SI) of digitoxin analogs of the present invention.

| Compound | $EC_{50}$ (nM) | $CC_{50}$ (nM) MTT | SI | $CC_{50}$ (nM) trypan blue |
| --- | --- | --- | --- | --- |
| digitoxin | 23.33 ± 0.67 | 2810.6 ± 668.0 | 120.46 | 5850 ± 1900 |
| α-L-amicetose | 3.77 ± 0.08 | 654.7 ± 177.0 | 173.61 | 4440 ± 1300 |
| Bis-L-amicetose | 14.78 ± 0.44 | 1119.7 ± 140 | 75.77 | 6800 ± 1100 |
| Tris-L-amicetose | 113.37 ± 2.86 | 2370.6 ± 278.3 | 20.91 | 9300 ± 1700 |

TABLE 2-continued

EC$_{50}$, CC$_{50}$ and selectivity index (SI) of digitoxin
analogs of the present invention.

| Compound | EC$_{50}$ (nM) | CC$_{50}$ (nM) MTT | SI | CC$_{50}$ (nM) trypan blue |
|---|---|---|---|---|
| α-D-amicetose | 37.50 ± 0.52 | 1105.05 ± 272.93 | 29.46 | |
| Bis-D-amicetose | 785.57 ± 37.28 | 12096.2 ± 718.3 | 15.40 | |
| Tris-D-amicetose | 2081.8 ± 93.4 | 14602.4 ± 1018.5 | 7.01 | |
| α-L-rhamnose | 4.77 ± 0.23 | 664.2 ± 184.6 | 139.25 | |
| Bis-L-rhamnose | 36.69 ± 0.91 | 1496.4 ± 573.4 | 40.78 | |
| Tris-L-rhamnose | 232.75 ± 3.88 | 6952.4 ± 859.6 | 29.87 | |
| α-D-rhamnose | 26.57 ± 0.88 | 2272.7 ± 551.2 | 85.52 | |
| Bis-D-rhamnose | 209.59 ± 5.98 | 6739.3 ± 717.4 | 32.15 | |
| Tris-D-rhamnose | 321.87 ± 11.67 | 9968.7 ± 1318.3 | 30.97 | |
| mannose | 7.31 ± 0.12 | 927.5 ± 376.9 | 126.79 | |

Example 3

Figure 3A:
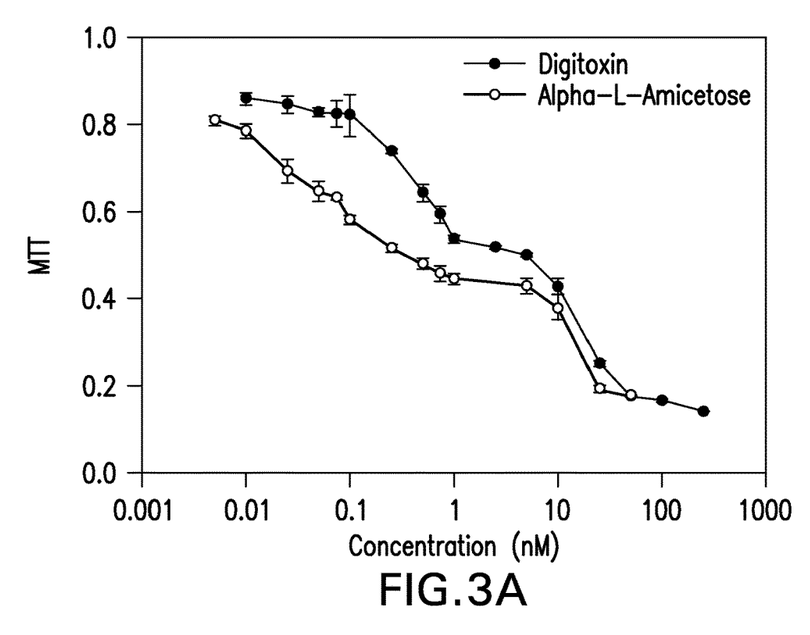
Figure 3B:
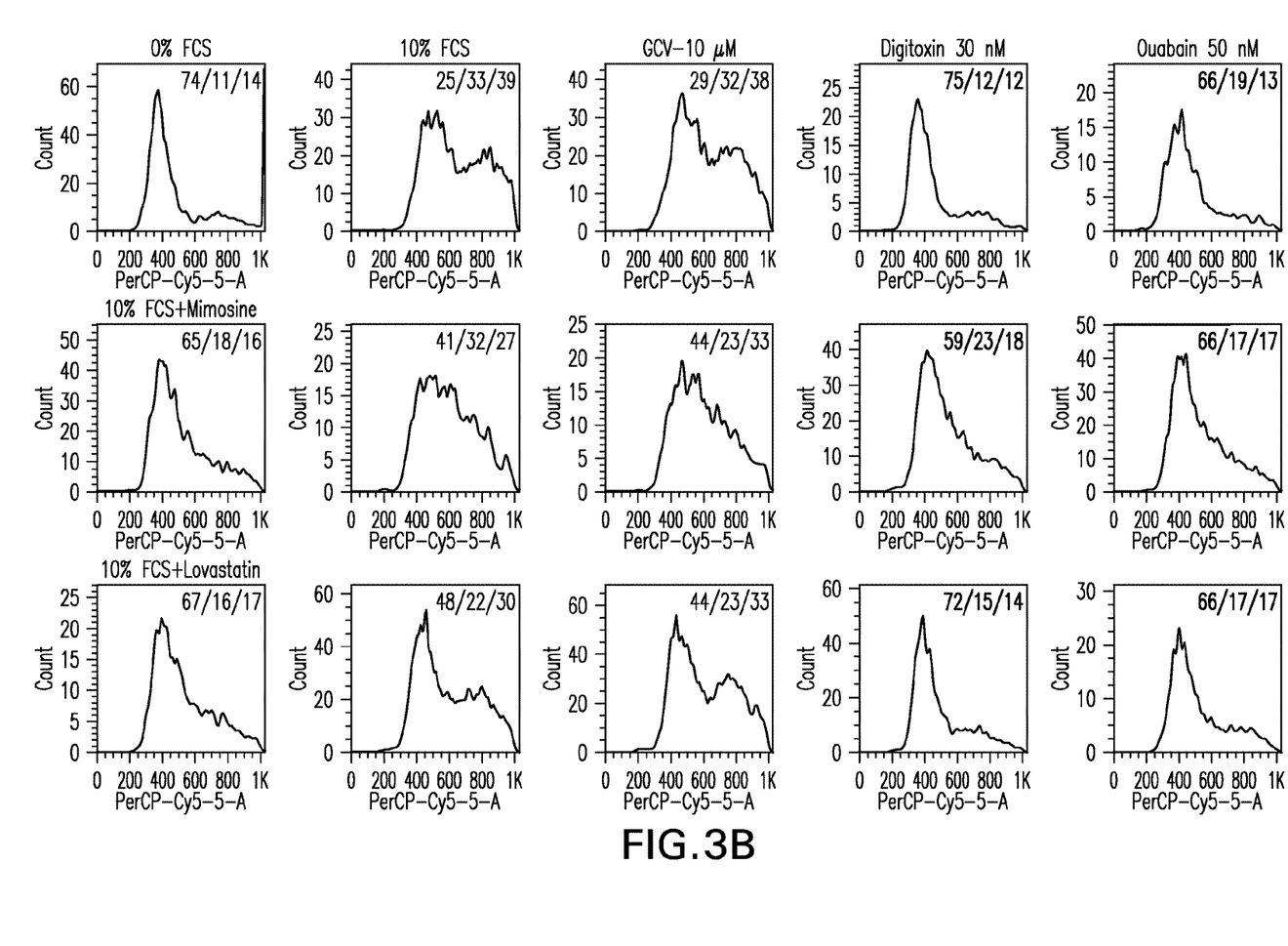

Evaluation of cell toxicity by MTT assay revealed that cell proliferation decreased to approximately 50% and remained at that level using higher concentrations of digitoxin analogs (FIG. 3A). The MTT assay may have overestimated cellular toxicity of digitoxin analogs in HFFs as a trypan blue assay showed higher CC$_{50}$ values (Table 2). The differences between the MTT and trypan blue assay complicated the calculation of antiviral selectivity. Shown in Table 2 are the SI based on the MTT CC$_{50}$. To further understand the effects of digitoxin analogs on cell proliferation/viability a cell cycle analysis was performed (FIG. 3B). After 3 day serum starvation cells were released from serum starvation, infected with Towne HCMV and treated with digitoxin or the cardiac glycoside ouabain for 24 hours. HFFs were stained with propidium iodide and subjected to cell cycle analysis by flow cytometry. The percentages of cells in G0/G1, S, and G2/M phases are indicated for each cell line. Cells treated with media including serum or GCV were used as control. Both digitoxin and ouabain arrested HFFs in G1, while cells treated with GCV or maintained in serum without compound showed normal cell cycle progression.

To understand how early in the cell cycle CGs arrested HFFs, cells were treated with mimosine (which arrests cells at mid G1) for 48 hours, then washed and treated for one day with digitoxin, ouabain or GCV (FIG. 3B). Digitoxin or ouabain could not relieve HFFs from cell cycle arrest induced by mimosine, while release from mimosine and treatment with GCV allowed the cells to normally progress in the cell cycle. A 48 hour pretreatment with lovastatin (an early G1 inhibitor) followed by release and 24 hour therapy with the compounds showed s similar pattern as pretreatment with mimosine (FIG. 3B). Taken together CGss arrest HFFs early in G1.

HCMV inhibition occurred prior to DNA replication, but following binding to its cellular receptors. Levels of IE, early and late viral proteins and cellular NF-κB were significantly reduced in HCMV-infected CGs-treated cells.

The unusual toxicity pattern of CGs in HFFs was noted. Cell viability was decreased to approximately 50% and then remained at that level even at high drug concentration. This pattern of cell viability as well as the effects of CGs on enzymes that depend on ATP led us to perform a live/dead staining procedure in addition to the metabolic assay to validate the results as well as cell cycle analysis. The limitation of the MTT assay, which is a metabolic assay, is that cellular metabolic activity can vary throughout the lifecycle of cells. MTT is cleaved by living and metabolically active cells; but the assay does not actually measure the number of viable cells in a culture, or their growth, but more a set of enzyme activities, that are related in various ways to the cellular metabolism.

The compositions and methods of the present invention show that improved anti-human herpes virus selectivity of novel digitoxin analogs can be achieved by modifying the sugar attached to the CG core structure. Digitoxin consists of digitoxigenin (pharmacophore) and the trisaccharide moiety, which is critical for its cardio-toxic and anti-cancer activity. Earlier studies suggested that an α$_2$-selective CG could result from sugar modification, because the structural differences in these isoforms are primarily in the extracellular carbohydrate binding loops. Digitoxin analogs with improved selectivity may have an important role in studies of CGs in human herpes virus-infected high-risk patients, thus, sugar modification may open the potential for discovery of new and safer digitoxin analogs.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for inhibition of human herpes virus replication in a subject comprising administering to the subject a therapeutically effective amount of a pharmaceutically acceptable composition comprising a compound of formula (I):

wherein R is one or two reducing sugars selected from the group consisting of a L-sugar, a D-sugar, a deoxy-sugar, a dideoxy-sugar, a glucose epimer, a substituted sugar, and a uronic acid, and pharmaceutically acceptable carrier.

2. A method for inhibition of human herpes virus replication in a cell or population of cells comprising administering to the cell or population of cells an effective amount of a composition comprising a compound of formula (I):

wherein R is one or two reducing sugars selected from the group consisting of a L-sugar, a D-sugar, a deoxy-sugar, a dideoxy-sugar, a glucose epimer, a substituted sugar, and a uronic acid.

3. The method of claim 1, wherein the reducing sugars are the same or different and are selected from the group consisting of L-amicetose, D-amicetose, L-rhamnose, D-rhamnose, L-ribose, D-ribose, L-fucose, D-fucose, 2-deoxy-D-galactose, 3-deoxy-D-glucose, 6-deoxy-D-glucose, 2-deoxy-2-fluoro-D-glucose, 6-deoxy-6-fluoro-D-glucose, L-lyxose, D-lyxose, L-rhamnose, L-allose, D-allose, L-altrose, D-altrose, L-galactose, D-galactose, L-xylose, D-xylose, D-gulose, L-mannose, D-mannose, L-idose, D-idose, L-mycarose, 6-keto-D-galactose, L-arabinose, D-arabinose, N-acetyl-D-galactosaminose, melibiose, lactose, maltose, D-galacturonose, L-talose, D-talose, 6-deoxy-6-azo-D-mannose, L-glucose, and D-glucose.

4. The method of claim 1, wherein R is 2 reducing sugars.

5. The method of claim 1, wherein R is selected from the group consisting of: α-L-amicetose, Bis-L-amicetose, α-D-amicetose, Bis-D-amicetose, α-L-rhamnose, Bis-L-rhamnose, α-D-rhamnose, Bis-D-rhamnose, and D-mannose.

6. The method of claim 1, wherein the composition is administered to the subject topically, subcutaneously, intravenously or orally.

7. The method of claim 1, wherein the pharmaceutical composition comprises at least one other active agent.

8. The method of claim 1, wherein the human herpes virus is selected from the group consisting of HHV-1, HHV-2, HHV-3, HHV-4, HHV-5, HHV-6A, HHV-6B, HHV-7, and HHV-8.

9. The method of claim 8, wherein the human herpes virus is HHV-5/HCMV.

10. A method for inhibition of the α3 subtype of the Na/K ATPase in a subject comprising administering to the subject a therapeutically effective amount of a pharmaceutically acceptable composition comprising a compound of formula (I):

wherein R is one or two reducing sugars selected from the group consisting of a L-sugar, a D-sugar, a deoxy-sugar, a dideoxy-sugar, a glucose epimer, a substituted sugar, and a uronic acid.

11. The method of claim 10, wherein the reducing sugars are the same or different and are selected from the group consisting of L-amicetose, D-amicetose, L-rhamnose, D-rhamnose, L-ribose, D-ribose, L-fucose, D-fucose, 2-deoxy-D-galactose, 3-deoxy-D-glucose, 6-deoxy-D-glucose, 2-deoxy-2-fluoro-D-glucose, 6-deoxy-6-fluoro-D-glucose, L-lyxose, D-lyxose, L-rhamnose, L-allose, D-allose, L-altrose, D-altrose, L-galactose, D-galactose, L-xylose, D-xylose, D-gulose, L-mannose, D-mannose, L-idose, D-idose, L-mycarose, 6-keto-D-galactose, L-arabinose, D-arabinose, N-acetyl-D-galactosaminose, melibiose, lactose, maltose, D-galacturonose, L-talose, D-talose, 6-deoxy-6-azo-D-mannose, L-glucose, and D-glucose.

12. The method of claim 11, wherein R is 2 reducing sugars.

13. The method of claim 10, wherein R is selected from the group consisting of: α-L-amicetose, Bis-L-amicetose, α-D-amicetose, Bis-D-amicetose, α-L-rhamnose, Bis-L-rhamnose, α-D-rhamnose, Bis-D-rhamnose, and D-mannose.

14. The method of claim 2, wherein the reducing sugars are the same or different and are selected from the group consisting of L-amicetose, D-amicetose, L-rhamnose, D-rhamnose, L-ribose, D-ribose, L-fucose, D-fucose, 2-deoxy-D-galactose, 3-deoxy-D-glucose, 6-deoxy-D-glucose, 2-deoxy-2-fluoro-D-glucose, 6-deoxy-6-fluoro-D-glucose, L-lyxose, D-lyxose, L-rhamnose, L-allose, D-allose, L-altrose, D-altrose, L-galactose, D-galactose, L-xylose, D-xylose, D-gulose, L-mannose, D-mannose, L-idose, D-idose, L-mycarose, 6-keto-D-galactose, L-arabinose, D-arabinose, N-acetyl-D-galactosaminose, melibiose, lactose, maltose, D-galacturonose, L-talose, D-talose, 6-deoxy-6-azo-D-mannose, L-glucose, and D-glucose.

15. The method of claim 2, wherein R is 2 reducing sugars.

16. The method of claim 2, wherein R is selected from the group consisting of: α-L-amicetose, Bis-L-amicetose, α-D-amicetose, Bis-D-amicetose, α-L-rhamnose, Bis-L-rhamnose, α-D-rhamnose, Bis-D-rhamnose, and D-mannose.

17. The method of claim 2, wherein the pharmaceutical composition comprises at least one other active agent.

18. The method of claim 2, wherein the human herpes virus is selected from the group consisting of HHV-1 HHV-6A, HHV-6B, HHV-7, and HHV-8.

19. The method of claim 18, wherein the human herpes virus is HHV-5/HCMV.

* * * * *